(12) United States Patent
Moore et al.

(10) Patent No.: US 7,223,370 B2
(45) Date of Patent: May 29, 2007

(54) DEVICE FOR FULLY AUTOMATED SOLID PHASE EXTRACTION

(75) Inventors: Thomas Moore, Drackendorf (DE); Uwe Naumann, Jena (DE); Wolfgang Kraemer, Jena (DE); Peter Zimmermann, Kahla (DE); Sebastian Pobering, Erfurt (DE); Holger Licht, Jena (DE); Gerd Ebert, Graitschen (DE); Ralf Thiericke, Jena (DE); Ingrid Schmid, Jena (DE)

(73) Assignee: CyBio AG, Jena (DE)

( * ) Notice: Subject to any disclaimer, the term of this patent is extended or adjusted under 35 U.S.C. 154(b) by 653 days.

(21) Appl. No.: 10/362,395

(22) PCT Filed: Aug. 20, 2001

(86) PCT No.: PCT/DE01/03147

§ 371 (c)(1),
(2), (4) Date: Jul. 16, 2003

(87) PCT Pub. No.: WO02/16906

PCT Pub. Date: Feb. 28, 2002

(65) Prior Publication Data

US 2004/0013572 A1 Jan. 22, 2004

(30) Foreign Application Priority Data

Aug. 24, 2000 (DE) .................. 100 43 345

(51) Int. Cl.
*B01L 3/02* (2006.01)
(52) U.S. Cl. .................. 422/100; 422/69; 422/70; 73/864.17; 73/864.24
(58) Field of Classification Search .................. 422/69, 422/70, 100; 73/864.17, 864.24, 864.25
See application file for complete search history.

(56) References Cited

U.S. PATENT DOCUMENTS

| 5,766,556 | A | | 6/1998 | DeWitt et al. | |
|---|---|---|---|---|---|
| 6,143,252 | A | * | 11/2000 | Haxo et al. | .................. 422/131 |
| 6,240,984 | B1 | * | 6/2001 | Fawcett et al. | .............. 141/130 |
| 6,506,611 | B2 | * | 1/2003 | Bienert et al. | .............. 436/180 |

FOREIGN PATENT DOCUMENTS

| DE | 25 30 015 | 1/1977 |
|---|---|---|
| DE | 38 05 808 | 9/1988 |
| DE | 197 49 557 | 5/1999 |
| DE | 198 35 833 | 2/2000 |

\* cited by examiner

*Primary Examiner*—Jan M. Ludlow
(74) *Attorney, Agent, or Firm*—Reed Smith LLP

(57) ABSTRACT

Device for automatically implementing the SPE method, with a two-dimensional needle arrangement which is suitable for removing substances from different two-dimensional specimen vessel arrangements and dispensing them under pressure into a two-dimensional cartridge arrangement.

3 Claims, 5 Drawing Sheets

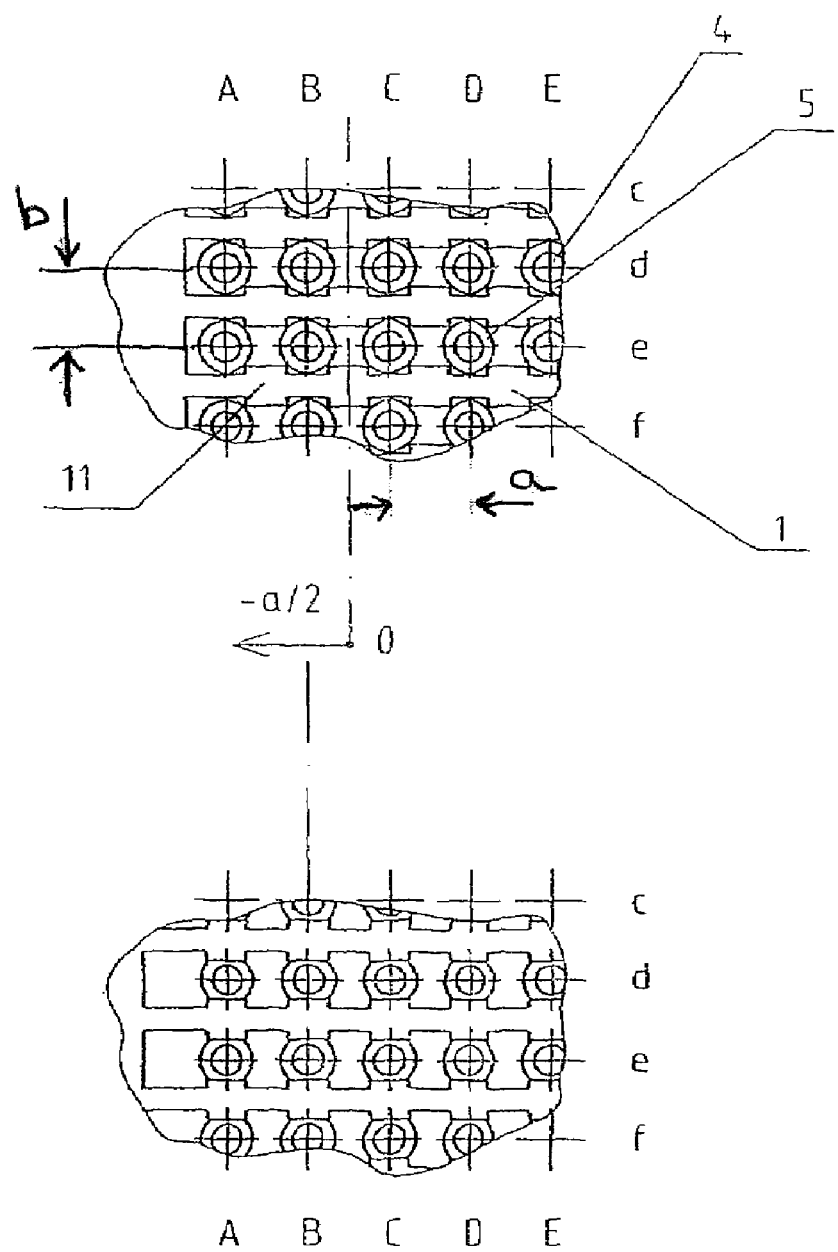
Fig. 1.1

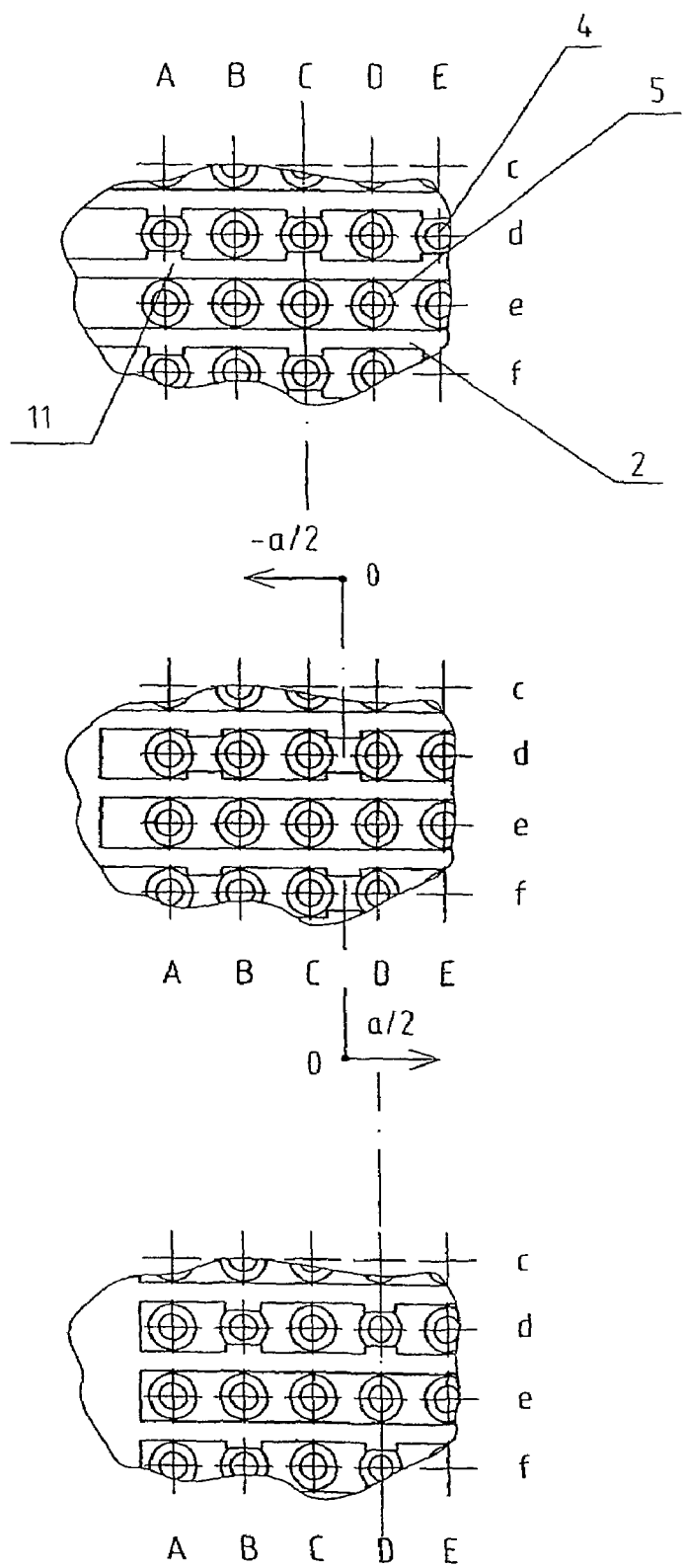
Fig. 1.2

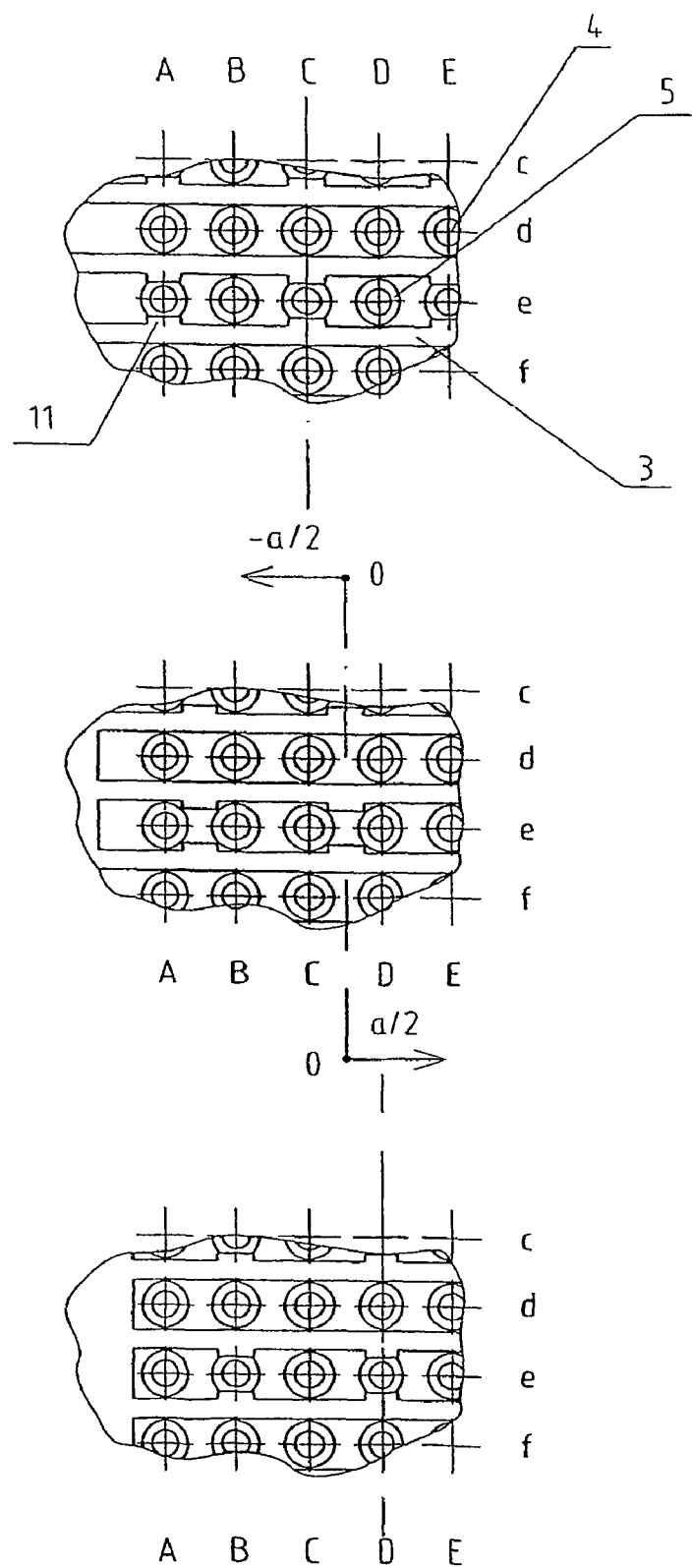
Fig. 1.3

DEVICE FOR FULLY AUTOMATED SOLID PHASE EXTRACTION

CROSS-REFERENCE TO RELATED APPLICATIONS

This application claims priority of international Application No. PCT/DE01/03147, filed Aug. 20, 2001 and German Application No. 100 43 345.6, filed Aug. 24, 2000, the complete disclosures of which are hereby incorporated by reference.

BACKGROUND OF THE INVENTION a) Field of the Invention

The process of solid phase extraction (SPE) makes it possible to separate complex mixtures of substances such as mixtures of microorganisms, vegetable and animal samples and synthetic mixtures containing combinatorial and parallelized syntheses for subsequent analysis. The separating process consists in that the complex substance mixture is initially adsorbed in suitable extraction phases, then separated by elution in one or more separation steps, each with one or more separation stages, and the obtained fractions are concentrated, if necessary, by another SPE step or are adjusted on a desired solvent.

b) Description of the Related Art

The complex work sequences for carrying out the process of solid phase extraction always comprise the same process steps, such as the conditioning of the extraction phases (sorbents, resins or separating phases), the supplying of specimens, washing, and elution. Identical process steps which sometimes run repeatedly in different sequences are excellent candidates for automation.

Since the supplied substances (specimens or solvents) do not flow through the extraction phase exclusively due to gravitational force in many applications, the substance is forced through the extraction phase by generating a vacuum below the extraction phase or an overpressure above the extraction phase. Technical apparatus has been developed for both principles. In this connection, systems making use of a vacuum suction technique have proven disadvantageous. The vacuum that can be generated remains limited to one bar and with a plurality of cartridges per vacuum channel the pressure compensation takes place through the best "running" cartridges (vessel containing an extraction phase), so that a complete elution often does not take place in poorly "running" cartridges. In particular With biological specimens, the viscosity and the particle proportion is often so unfavorable that some cartridges elute incompletely when the process is carried out simultaneously in a plurality of cartridges with the vacuum suction technique (e.g., *Nachr. Cheni. Tech. Lab.* 44; 1969; No. 4; page M18).

In known devices which press the specimen through the extraction phase with overpressure, each cartridge is individually sealed independently from one another. For example, the STRATEC Elektronik GmbH company offers an automatic pipettor, known as VIVACE, with an expansion module FEX which is suitable for carrying out the SPE process. In order to generate a positive pressure on the extraction phase, an appropriate tool of one of the two pipetting arms of the VIVACE is placed on the upper end of the column (cartridge end) in a gastight manner and the necessary pressure is built up with a suitable inert gas. Each of the two pipetting arms is outfitted with a pipetting needle. The pipetting needle can be freely positioned within a plane by means of the linear adjustment of the pipetting needle at the pipetting arm in one coordinate direction and the movement of the pipetting arm in a coordinate direction vertical to the latter. In this way, pipetting can be carried out from virtually any commonly used vessel. Regardless of the circumference of the vessels or the distances at which they are positioned from one another below the pipetting arm, the pipetting tip can be moved to the vessels in such a way that it stands above the vessels exactly in the center.

The demand for the use of vessels with different circumferences results from the different volumes which depend, for example, on their concentration to be taken up and dispensed by means of the pipetting needles. For an economical use of substances and a reproducible volume take-up, the entire volume to be taken up must be taken up by completely emptying a vessel. Since the relative lift required for this purpose between the pipetting needle and vessel bottom should be as small and as constant as possible regardless of the capacity of the vessel, there is a demand for the use of vessels of the same height with different circumferences having correspondingly different capacities. However, vessels for dispensing the substance—even if they have different capacities—could also, in principle, have the same circumference but a different height because immersion is not required for dispensing in the vessel. However, for automation, a constant lift is also advantageous in this case, so that there is also a demand in this case for the possibility of using vessels with different circumferences.

Vessels for receiving (specimen vessels) and dispensing (cartridges) are available as individual vessels, also already arranged in a rack in a two-dimensional arrangement with modular sizes or grid dimensions (center distances) of a×b (a represents the grid dimension of vessels arranged in a row and b represents the grid dimension of the vessels arranged in a column).

As an alternative to the two-dimensional arrangement of individual vessels, there are monolithic blocks of specimen vessels and cartridges in which the actual vessels are formed by chambers with grid dimensions a×b.

The cross section of the individual vessels and chambers is usually round or rectangular. Polygonal shapes are also known. In arrangements with round and square cross sections: a=b.

The grid dimensions are adapted to those of commercially available microtiter plates or other multi-vessel systems.

With regard to the automation of simultaneous receiving and dispensing of specimens from and into vessel arrangements of different grid dimensions, there is the particular problem of providing a needle arrangement which is suitable for emptying and filling these vessels and which can also be sealed relative to these vessels.

The prior art does not disclose any apparatus for carrying out the SPE method that is suitable for receiving the substances from two-dimensional arrangements of specimen vessels of different grid dimensions with a two-dimensional needle arrangement and dispensing the substances in a two-dimensional cartridge arrangement under pressure.

OBJECT AND SUMMARY OF THE INVENTION

It is the primary object of the invention to provide a device with a two-dimensional needle arrangement which is suitable for removing substances from a two-dimensional arrangement of specimen vessels or specimen vessel chambers and dispensing them into a two-dimensional arrangement of cartridges or cartridge chambers under pressure. The arrangement of the specimen vessels or specimen vessel chambers and cartridges or cartridge chambers should advisably comprise 96, 48 or 24 cartridges or cartridge chambers whose relative grid dimensions are equal to the grid dimension of commercially available 96-well microtiter plates, 48-well or 24-well multi-vessel systems with the surface area of microtiter plates. Further, it should be possible to receive other substances through each individual needle or needle groups.

This object is met for a device for the automatic implementation of the SPE method according to the preamble of claim 1 substantially in that there is a two-dimensional needle arrangement with grid dimensions a×b from which needle groups are formed by means of a selection mechanism, with grid dimensions equal to a and b or a multiple of a and b, so that these needle groups are coupled with a vertical drive and can be selectively lowered for receiving substances. The grid dimensions can be an equal or unequal multiple of a in the column and line direction, which results from the use of specimen vessels or specimen vessel chambers with a rectangular cross section. In order to introduce the received substance into the cartridges under pressure, there is a cartridge seal which seals the upper openings of the cartridges or cartridge chambers, even with different cross sections, with a planar seal and a radial seal toward the circumference of the needles.

The invention will be described more fully in the following with reference to the drawings.

BRIEF DESCRIPTION OF THE DRAWINGS

In the drawings:

FIG. 1 shows the different positions of the register rails of a selection mechanism relative to the needles of the needle arrangement;

FIG. 2 shows a section from a device interacting with a cartridge block with grid dimensions a×a; and FIG. 3 shows a section from a device interacting with a cartridge block with grid dimensions 2a.

DESCRIPTION OF THE PREFERRED EMBODIMENTS

Figure 2:
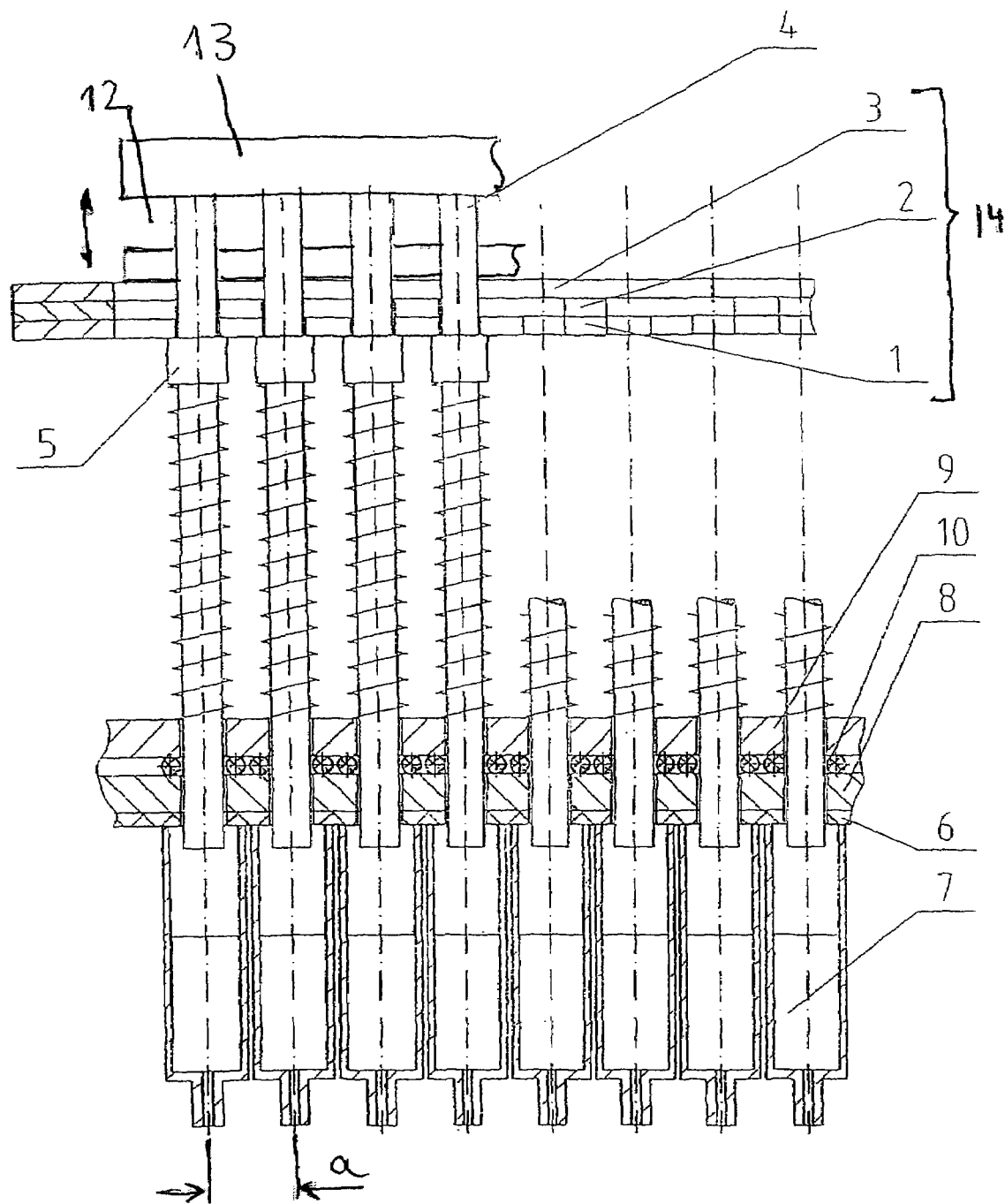

A device according to the invention for automatic implementation of the SPE method is one that can be described well, based on the different functions, as a combination of a plurality of different modules. In addition to the modules essential to the invention, the selection mechanism and cartridge sealing, there are other modules derived from the prior art that were optimized with knowledge of the art for a device according to the invention. This concerns the entire needle head with vertical needle drive unit, lifting and transporting device for vessels such as the reservoir and waste container, racks with specimen vessels or cartridges such as microtiter plates and other multi-vessel systems in microtiter plate format such as specimen vessel blocks or cartridge blocks, as well as storage units such as stackers, stacker carrousels or so-called hotels for the above-mentioned vessels.

A two-dimensional needle arrangement which is movable vertically by means of a vertical needle drive and preferably has 96 needles arranged in an 8×12 grid with grid dimensions a×a equal to the grid and the grid dimensions of a 96-well microtiter plate is essential to the function of the device. Every individual needle, in connection with a tube system, a reservoir and a pump injector, forms an injection system. A plurality of injection systems can be connected with a drive unit or each injection system can be connected with its own drive unit. In a corresponding manner, volume can be taken up in all injection systems simultaneously or by groups or only in individual injection systems. For monitoring pressure, every injection system has a pressure sensor and a valve which can open the system to the atmosphere relative to normal pressure. The pressure injection itself displaces air or a gas. The reservoir is protected from the pressure injection by an injection protector and an aerosol filter.

The vertical needle drive is coupled with the needles by a selection mechanism. Depending on the position of the selection mechanism, different needle groups are coupled with or uncoupled from the vertical needle drive.

In the practical embodiment example, a first needle group is formed by all needles (8×12), i.e., the needle group has the grid dimensions a×a (a is equal to the grid dimension of a 96-well microtiter plate), the second to fifth needle groups are formed by 24 needles (4×6) in each instance. These 24-needle groups have grid dimensions of 2a×2a, which is achieved in that only every second needle is coupled in every direction of the needle arrangement. The larger grid dimension makes it possible to take up and dispense in vessels with a large cross section.

In other embodiment forms, the selection mechanism can also be designed in such a way that 6-needle groups are formed with a grid dimension of 4a×4a, 12-needle groups are formed with the grid dimension of 2a×4a, and so on.

An advantageous construction for a selection mechanism will be described more fully in the following. A stack of three register rails which are located one on top of the other and are displaceable in column direction is inserted between the columns formed by twelve needles 4. Each stack comprises a first register rail 1 at which twelve driver projections 11 are formed across from one another along the length of the register rail 1 on both sides with a width of less than a/2 and with a grid dimension a relative to one another, and further comprises a second and third grid rail 2; 3 with four driver projections 1 of the same width as the first grid rail 1 and formed with a grid dimension of 2a relative to one another on one side. The first register rails 1 are connected with a first drive unit, the second register rails 2 are connected with a second drive unit, and the third register rails 3 are connected with a third drive unit, The register rails 1; 2; 3 are positioned relative to one another in such a way that one of the five needle groups is coupled by the selective control of the three drive units, each of which causes a step of length a/2 in an opposite direction proceeding from a zero position. The coupling takes place in that two driver projections 11 contact a collar 5 formed at each one of the needles 4 for this purpose.

FIGS. 1.1 to 1.3 show the possible positions of the individual register rails. FIG. 1 shows the first register plane in which the first register rails 1 are positioned in a zero position and in a position which is displaced by a half grid measure a/2. While the driver projections 11 do not contact any needles 4 in the zero position, all driver projections 11 contact a collar 5 of a needle 4 in the position that is displaced by a/2, so that all needles 4 are coupled by two driver projections 11. At the same time, the second and third register rails 2, 3 are located in their rest positions. In order to lower one of the 24-needle groups, the first register rails 1 must be moved back to their zero position and the second and third register rails 2, 3 must be brought into engagement with needles 4. Due to the mirror-symmetric positioning of the register rails 2, 3 in the second and third register planes, as is shown in FIGS. 1.2 and 1.3, every second needle 4 of every second column is coupled after the displacement of the register rails 2, 3 from the zero position by a/2 or −a/2.

This means that when the second register rails 2 are displaced by a/2 and the other register rails 1, 3 are located in their zero position, the needles 4 are coupled with coordinates B:d; D:d; B:f; D:f, and so on. When displaced by −a/2, the needle group is correspondingly coupled with the needles 4 of coordinates A:d; C:d; A:f, C:f, and so on. A coupling of the needles 4 of columns c and e is caused in an analogous manner with the positioning of the third register rails 3. Instead of the three drive units mentioned above, one or two drive units which selectively drive the register rails can also be provided.

The described selection mechanism is an advantageous, robust construction and enables a quick and reliable formation of needle groups. FIG. 2 shows the positioning of the selection mechanism relative to the needles 4 and the construction of the collar 5 at the needles viewed from the side.

The cartridge seal (FIG. 2) is located below the needle arrangement. The object of this cartridge seal is to seal a cartridge block 7 positioned below it relative to the circumference of the needles 4 of the needle arrangement. It comprises two functionally independent seals, a planar seal and a radial seal. The planar seal is formed by a sealing plate 6 whose outer dimensions are adapted to the outer dimensions of a cartridge block 7 and which is provided with an arrangement of 96 holes arranged with grid dimensions of a×a relative to one another. The sealing plate 6 which is made of an elastomer, for example, is fixedly connected to a first pressure plate 8 which, like a second pressure plate 9 arranged above it, has the same hole arrangement as the sealing plate 6.

The holes have a diameter which is greater than the needle diameter so that the needles 4 can be guided through the plates without obstruction.

The entire cartridge seal is vertically movable in order to lift it from the cartridge block 7 or place it on the latter. Further, the second pressure plate 9 is displaceable toward the first in order to deform O-rings 10 which are located between the two pressure plates 8; 9 and each of which encloses a needle 4. The inner diameter of the O-rings 10 becomes smaller as the distance between the pressure plates becomes smaller due to the increasing pressure and accordingly seals the needles 4 at their circumference.

One or two drive units can be provided for the vertical movement of the entire cartridge seal and the second pressure plate 9 inside the cartridge seal.

In a second embodiment form of a cartridge seal that is not shown in the drawings, the radial sealing that is generated by mechanical pressure in the previously described embodiment example is generated by pneumatic pressure. The second pressure plate 9 which is constructed analogous to the described embodiment example in other respects is arranged at a fixed distance from the first pressure plate 8. A pressure chamber in which an overpressure is generated by a compressed air control is located between the two pressure plates 8, 9. Ninety-six tubes through which the needles 4 are guided run through this chamber. As the overpressure in the chamber increases, the tubes make tight contact around the needles 4 and seal the needles 4 at the circumference. In order to loosen the vertical seal, the pressure chamber is opened or a vacuum is applied.

After sealing the cartridge block, the substance which was previously received by the needles 4 is pressed through the extraction phases located in the cartridges by means of overpressure.

The modules of the whole device which were not described more fully such as the lift-out and transport device and storage units provided for depositing and storing the variety of vessels are known in principle from the prior art and are only optimized for a device according to the invention in a manner known to the person skilled in the art.

All vessels from which substances are received or in which substances are dispensed must be arranged relative to one another in grid dimensions a×a or in a multiple of a, provided they do not have an opening greater than that of the surface formed by the needle arrangement, so that the substance can be received and/or dispensed in a defined manner by a needle group.

These vessels are advantageously specimen vessel chambers or cartridge chambers of specimen vessel blocks or cartridge blocks. The blocks can be injection molded parts whose surface area corresponds with respect to its outer dimensions to a microtiter plate and whose chambers have a round or rectangular cross section.

Blocks of this kind are particularly suitable because the upper openings of the vessels compulsorily lie in a plane and a uniform planar sealing is accordingly possible without further steps.

It is less suitable but possible in principle that the vessel arrangement is formed by individual vessels which are positioned above the arrangement in a rack relative to one another with grid dimension a×b or a multiple of a and b. The vessels for receiving can have a rectangular cross section or a round cross section since only one needle is lowered centrally per vessel by means of the selection mechanism.

When dispensing under pressure in cartridges or cartridge chambers, on the other hand, a round cross section could be problematic at least when arranged in grid dimensions unequal to a×b. In this case, when the cartridge seal is placed on the upper openings of the cartridges at which a collar is formed in principle, it must be ensured by way of the dimensioning of the diameter that all holes of the sealing plate lie within the inner cross section of the cartridges in order to guarantee reliable sealing.

Figure 3:
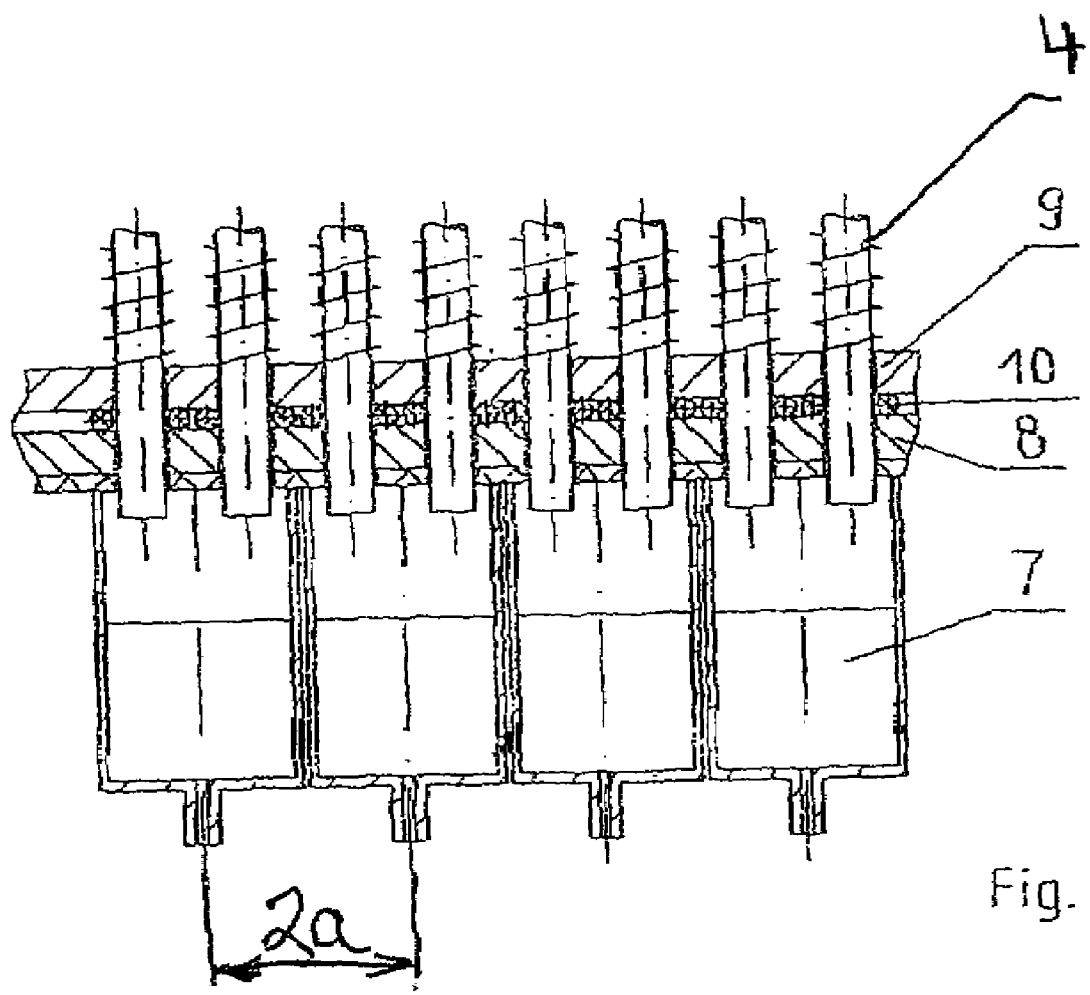

When using a cartridge block with grid dimensions a×a, it can be seen clearly from FIG. 2 that one of the needles 4 projects through the cartridge seal into a cartridge chamber. When the grid dimensions of the cartridge block are equal to 2a×2a as is shown in FIG. 3, four needles 4 project into a cartridge chamber. The cartridge chambers can be filled under pressure by means of all four needles 4 or by means of fewer, or only one needle 4, since the individual needles 4 with their respective injection systems represent a pressure-tight closed formation in themselves.

While the foregoing description and drawings represent the present invention, it will be obvious to those skilled in the art that various changes may be made therein without departing from the true spirit and scope of the present invention.

REFERENCE NUMBERS a grid dimensions of the needles arranged in a row
b grid dimensions of the needles arranged in a column
1 first register rail
2 second register rail
3 third register rail
4 needle
5 collar
6 sealing plate
7 cartridge block
8 first pressure plate
9 second pressure plate 9. O-ring
10. driver projections
11. vertical drive unit
12. needle head
13. selection mechanism

The invention claimed is:

1. A device for automatically implementing the SPE method, comprising:
    a vertical drive unit;
    needles which are connected to said vertical drive unit and by which liquid substances or liquids with substance particles are received from specimen vessels and dispensed in cartridges;
    said needles being arranged at a needle head in a two-dimensional arrangement with grid dimensions a×b;
    said specimen vessels and cartridges adapted to being positioned relative to one another in a two-dimensional arrangement with grid dimensions a×b or with a multiple of a and b below the needle head;
    a selection mechanism by which different needles forming a needle group are selectively coupled with the vertical drive unit;
    said different needle groups being formed by needles with the grid dimensions a×b or a whole number multiple of a and/or b; and
    a cartridge seal which is formed by two functionally independent seals, a planar seal and a radial seal and which seals the cartridges toward the circumference of the needles belonging to the needle groups, so that the substance is dispensed under pressure into the cartridge, wherein the selection mechanism has register rail blocks equal to the quantity of needles arranged in one direction, each of these register rail blocks is arranged in this direction in the same plane between and adjacent to the needles, which register rail blocks comprise at least three register rails at which driver projections are formed relative to one another in a grid dimension equal to that of the needles arranged in this direction or to a multiple thereof, wherein the drive projections selectively contact a collar of a needle by means of the displacement of the register rails and accordingly link the respective needle to the vertical drive unit.

2. The device for automatically implementing the SPE method according to claim 1, wherein every register rail block comprises a first, a second and a third register rail, wherein the driver projections of the first register rail are formed in a grid dimension a equal to that of the needles arranged in this direction and the driver projections of the second and third register rails are formed relative to one another in the grid dimension 2a, and all first register rails are connected to a first drive unit, all second register rails are connected to a second drive unit, and all third register rails are connected to a third drive unit, which drive unit displaces the register rails selectively by a step of length a/2 from a zero position in alternate directions.

3. The device for automatically receiving and dispensing liquids or liquids with substance particles comprising:
    a vertical drive unit;
    needles which are connected to said vertical drive unit and by which liquid substances or liquids with substance particles are received from specimen vessels and dispensed in cartridges;
    said needles being arranged at a needle head in a two-dimensional arrangement with grid dimensions a×b;
    said specimen vessels and cartridges adapted to being positioned relative to one another in a two-dimensional arrangement with grid dimensions a×b or with a multiple of a and b below the needle head;
    a selection mechanism by which different needles forming a needle group are selectively coupled with the vertical drive unit;
    said different needle groups being formed by needles with the grid dimensions a×b or a whole number multiple of a and/or b; and
    wherein the selection mechanism has register rail blocks equal to the quantity of needles arranged in one direction, each of these register rail blocks is arranged in this direction in the same plane between and adjacent to the needles, which register rail blocks comprise at least three register rails at which driver projections are formed relative to one another in a grid dimension equal to that of the needles arranged in this direction or to a multiple thereof, which drive projections selectively contact a collar of a needle by means of the displacement of the register rails and accordingly link the respective needle to the vertical drive unit.

* * * * *